(12) United States Patent
Nistler et al.

(10) Patent No.: US 7,239,141 B2
(45) Date of Patent: Jul. 3, 2007

(54) MAGNETIC RESONANCE APPARATUS AND GRADIENT COIL/RADIO FREQUENCY UNIT THEREFOR WITH FRACTURE-RESISTANT ELECTRICAL CONNECTIONS

(75) Inventors: Jürgen Nistler, Erlangen (DE); Wolfgang Renz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/340,216

(22) Filed: Jan. 26, 2006

(65) Prior Publication Data
US 2006/0208736 A1    Sep. 21, 2006

(30) Foreign Application Priority Data
Jan. 26, 2005 (DE) .................. 10 2005 003 670
Dec. 8, 2005 (DE) .................. 10 2005 058 651

(51) Int. Cl.
*G01V 3/00* (2006.01)
(52) U.S. Cl. ........................ 324/318; 324/309
(58) Field of Classification Search ........... 324/318, 324/319, 322, 309, 307, 300; 600/410–422
See application file for complete search history.

(56) References Cited

U.S. PATENT DOCUMENTS

| | | | |
|---|---|---|---|
| 5,594,339 A * | 1/1997 | Henderson et al. | 324/318 |
| 5,864,235 A * | 1/1999 | Moritz et al. | 324/318 |
| 6,842,005 B2 | 1/2005 | Schuster | |
| 6,925,322 B2 * | 8/2005 | Helfer et al. | 600/423 |
| 6,930,482 B2 | 8/2005 | Heid et al. | |
| 7,030,610 B2 * | 4/2006 | Mansfield | 324/318 |
| 7,068,035 B2 * | 6/2006 | Nistler et al. | 324/322 |

* cited by examiner

*Primary Examiner*—Brij B. Shrivastav
(74) *Attorney, Agent, or Firm*—Schiff Hardin LLP

(57) ABSTRACT

A magnetic resonance apparatus has an integrated gradient and radio frequency coil unit that includes at least one antenna rod with a conductor and a gradient coil unit. At least one electrical connection exists between the conductor and an electrical contact region arranged at an adjoining region of the gradient coil unit. The electrical connection is formed by a flexible circuit board that is electrically connected both with the conductor and with the contact region. Such an electrical connection of the antenna rod is insensitive to strong vibrations.

20 Claims, 2 Drawing Sheets

MAGNETIC RESONANCE APPARATUS AND GRADIENT COIL/RADIO FREQUENCY UNIT THEREFOR WITH FRACTURE-RESISTANT ELECTRICAL CONNECTIONS

BACKGROUND OF THE INVENTION

1. Field of the Invention

The present invention concerns a magnetic resonance apparatus of the type having an integrated gradient and radio frequency coil unit, the gradient and radio frequency coil unit includes at least one antenna rod with a conductor and a gradient coil unit, with at least one electrical connection between the conductor and an electrical contact region located at an adjoining region of the gradient coil unit. The invention also concerns such a gradient and radio frequency coil unit.

2. Description of the Prior Art

Magnetic resonance technology is a known modality to, among other things, acquire images of the inside of a body of an examination subject. Rapidly-switched gradient magnetic fields are superimposed on a static basic magnetic field that is generated by a basic field magnet in a magnetic resonance apparatus (MR apparatus). These rapidly-switched gradient magnetic fields are generated by a gradient coil unit. To excite MR signals, radio frequency signals (RF signals) are radiated into the examination subject with a radio frequency antenna. Integrated gradient and radio frequency coil units are used in order to minimize the space requirement of the gradient coil unit and the radio frequency antenna. These integrated gradient and radio frequency coil units are subject to strong vibrations in operation. This can lead to damaging of components, for example to interruption of a solder contact. This danger exists in particular for the connection of antenna elements to the gradient coil unit or to the radio frequency shield (RF shield) mounted at that location.

In a hollow-cylindrical MR apparatus, the gradient coil unit is fashioned such that a gap or open space in which the antenna rods are arranged exists in the midway along in the axial direction. Radio frequency currents that generate the radio frequency field flow through these connections. The gradient coil units typically are at least partially jacketed by the RF shield. The antenna rods are sealed with the integrated gradient coil unit in a pouring method. In the operation of the MR apparatus, relative to the antenna rod the gradient coil now vibrates with amplitudes in the micrometer range. The movement/vibrations of the antenna rods relative to the RF shield that is sealed with the gradient coil lie in the frequency range of up to approximately 4 kHz given a maximum amplitude (deflection) of about 10 µm in the frequency range around 900 Hz.

The connection of the antenna rods to the RF shield is stressed due to the relative movement. The type of the electrical connection has the purpose of an optimally low-inductivity and low-loss connection. Wide solder bands that are rigidly soldered both on the circuit board and on the shield are used for this purpose. The rigid soldering is also achieved with electrical components (for example an RF choke), these being additionally secured by adhesion.

It is generally necessary for the electrical connection to have an optimally small influence on the antenna properties (no detuning effect, high frequency stability, etc.

A reinforced or rigid connection is most advantageous from an electrical point of view. The connection as part of the antenna influences the tuning of the antenna interim of performance and the resonance frequency. The effective inductivity of the connection (which should be optimally low) as well as the losses in the connection are of decisive importance. Overall the properties of the connection should not be changed by the vibrations or movements.

Such connections exhibit disadvantages. For example, if "thick" copper (for example 1 mm) is used for the connection, the connection at the solder points on the circuit board or the RF shield can crack or break since there only copper thicknesses of 9 µm or 18 µm must be used in order to suppress gradient eddy currents. If "thinner" copper band (0.1 . . . 0.2 mm) is used, cracks can occur within the connection.

Various measures have been proposed to reduce the vibrations in order to be able to maintain such a "rigid" solution. The surfaces of the RF shields are treated in order to improve the connection with the sealing compound [pottant] and to increase the bonding overall. Furthermore, reinforcement anchors (reinforcement ties; stiffening ties) can be installed on the circuit boards/RF shields and additionally through the RF shields—the latter being possible only in a limited manner since the RF shield cannot be permeable. The rigidity of the gradient coil also can be increased by the introduction of glass and glass fiber reinforced plastic rods. All of these measures still do not achieve the desired reliability of the electrical connection.

SUMMARY OF THE INVENTION

An object of the invention is to reduce the disadvantageous effects of the vibrations on the electrical connection of the antenna rod, i.e. to ensure the mechanical endurance and simultaneously to guarantee that no change of the antenna properties occurs due to the vibrations.

The above object is achieved in accordance with the principle of the present invention in a magnetic resonance apparatus having a gradient and radio frequency coil unit with at least one antenna rod and a conductor and a gradient coil unit, and at least one electrical connection between the conductor and an electrical contact region of the gradient coil unit formed by a flexible circuit board that is electrically connected with the conductor and with the contact region.

The solution is based on the surprising technical effect that, despite the flexible element, the antenna circuit (in particular given suitable selection of the coating and circuit board thickness) is not influenced in terms of its properties, and the electrical connection satisfies the high requirements:

Vibration resistance

Low inductivity for the RF antenna

Slight losses (current amplitudes up to 30 A per antenna rod

No influencing and heating due to gradient eddy currents

No changes of the antenna properties occur due to vibration and movement of the antenna Use under cramped space relationships The connection in accordance with the invention foregoes a mechanically-rigid solder connection, and instead makes use of the elastic properties of flexible circuit boards. The flexing properties of the flexible circuit boards give the electrical connection a spring-like elasticity that protects the solder points from damage, even given strong vibrations over a longer span of time. Electrical circuits (for example an antenna circuit or a detuning circuit) are thereby electrically connected with the contact regions. The contact region is located near an antenna rod; for example, it is arranged on the gradient coil unit (acting as a carrier) such as, for example, on conductor traces (runs) applied there or on the RF shield of the gradient coil itself when this is, for example, part of the RF circuit.

In one embodiment of the invention, a conductor of an antenna circuit on the antenna rod is electrically connected with the RF shield via a flexible circuit board. In another embodiment, a contact of an energy supply line of one detuning circuit is electrically connected with an electrical contact of the detuning circuit which is likewise located on the antenna rod, likewise via a flexible circuit board.

Depending on the current flow along the flexible circuit board, the width and thickness of the circuit board is adjusted such that an excessive heating is avoided.

The radius of curvature of the circuit board is selected such that the stress for a copper coating as well as for the carrier plate is optimally small and insensitive to vibrations.

Due to the inventive electrical connection with the flexible circuit board, it is possible to countersink electrical components (in particular a choke of the detuning circuit) at least partially in an antenna circuit board and in particular to cement said electrical components with the antenna circuit board, such that these electrical components are exposed only to reduced vibrations.

DESCRIPTION OF THE PREFERRED EMBODIMENTS

Figure 1:
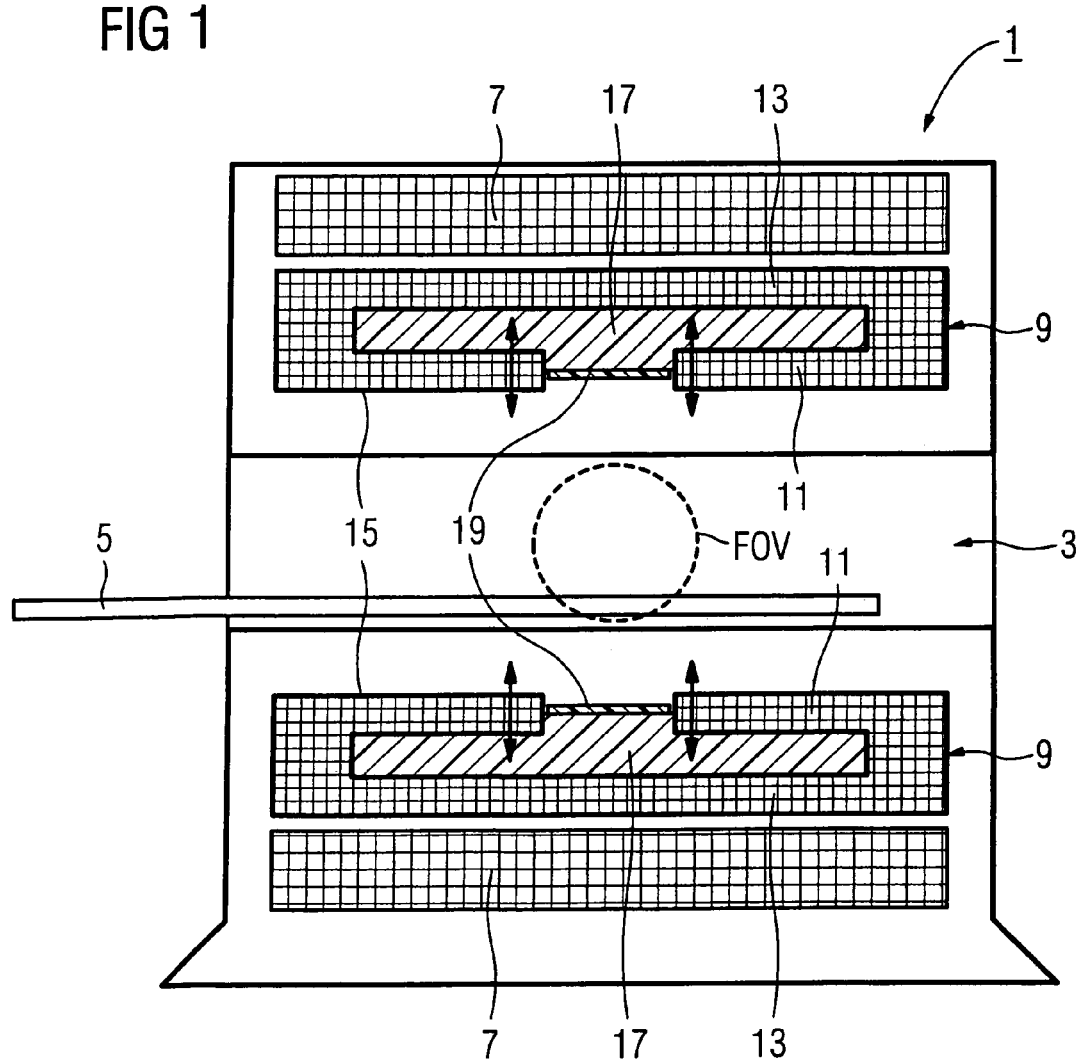
FIG. 1 is a section through an MR apparatus with an integrated gradient and radio frequency coil unit.

FIG. 1 shows a magnetic resonance apparatus 1 with a cylindrical acquisition region 3 for a patient who (with a patient bed 5) is positioned with a region to be examined in the examination region FOV of the magnetic resonance apparatus. A homogeneous basic magnetic field that is generated by a basic field magnet 7 is present in the examination region FOV. A radio frequency signal is radiated into the examination region FOV to excite magnetic resonance signals. Spatial coding is possible by the superimposition of gradient magnetic fields with the basic magnetic field. The gradient magnetic fields and the RF field are generated with an integrated gradient and radio frequency coil unit 9. The gradient and radio frequency coil unit 9 includes a primary gradient coil 11, a secondary gradient coil 13, and an RF shield 15 essentially surrounding the coil units and that also lines a field return chamber 17. The field return chamber 17 is filled with filling material and casting resin, in which antenna rods 19 in a central region are arranged and fixed.

A central, annular region is not required by conductors of the primary gradient coil 11. The antenna rods 19 are azimuthally distributed in this annular free space and represent the connections for radio frequency currents between regions of the RF shield 15. The associated field lines of the RF field close in the field reflux chamber 17.

Figure 2:
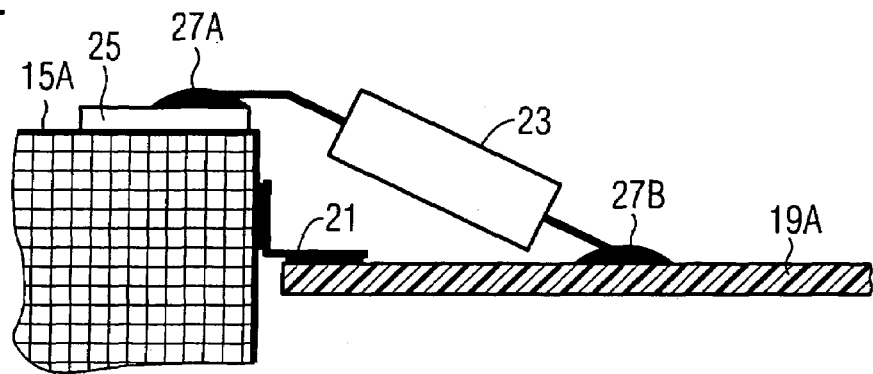
FIG. 2 is a detailed view of the solution according to the prior art.
Figure 3:
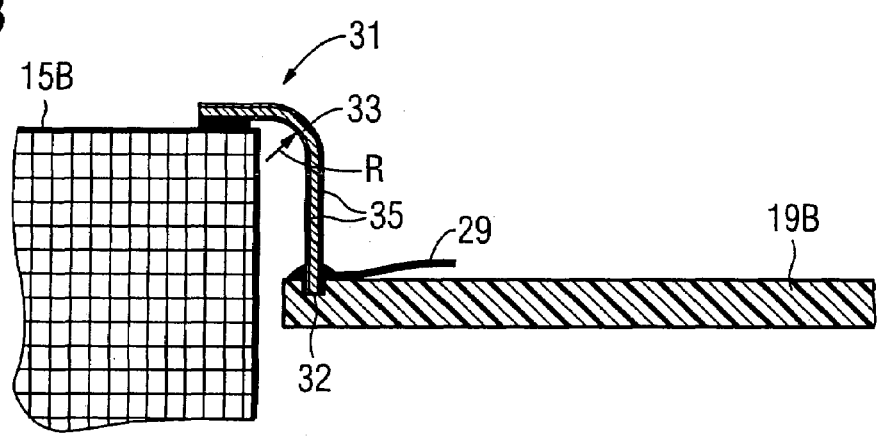
FIG. 3 illustrates the inventive use of a flexible circuit board in the connection of an antenna rod with the radio frequency shield of the gradient coil unit.
Figure 4:
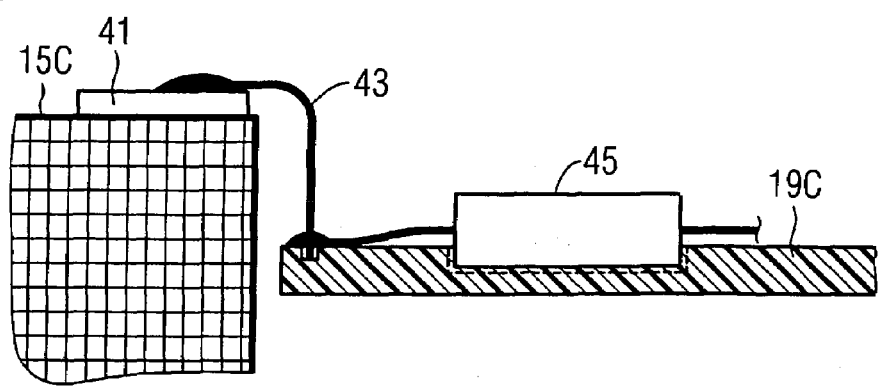
FIG. 4 shows the use of a flexible circuit board in the electrical supply of a detuning circuit.

In a detailed view, FIGS. 2 through 4 respectively show the transition region from the antenna rods 17 to the radio frequency shield 15.

For example, there are also similar transition regions given integrated gradient and RF coil units in open MR apparatuses that, for example, are fashioned disc-shaped.

FIG. 2 shows the known technique for connection of antenna conductors on an antenna rod 19A by means of a rigid solder connection 21 executed at an angle. Furthermore, it is shown how a choke 23 is, for example, rigidly soldered with a conductor trace 25, whereby the conductor trace 25 runs electrically-insulated on a radio frequency shield 15A. The connection of the choke 23 with a detuning circuit also ensues via a rigid solder connection 27B. The solder points 21 and 27A, 27B are potential weak points; for example, breakages (fracture) can form in the solder connections.

FIG. 3 shows an example of the connection of an antenna conductor 29 on an antenna rod 19B with an RE shield 15B. The connection to the RF shield 15B is produced by one or more flexible circuit boards 31. The flexible circuit board 31 is soldered in an internally lined longitudinal slit 32 of the antenna rod 19B. The other end of the circuit board 31 is soldered with the RF shield 15B of the gradient coil unit. The distance of the longitudinal slit from the RF shield 15B is approximately 5 mm and the radius of curvature R is likewise 5 mm. In order to keep the inductivity low, a number of these flexible circuit boards are used in parallel, with each of the circuit boards exhibiting a width of less than 10 mm, such as approximately 8 mm. In an embodiment, the flexible circuit board 31 has a carrier material made from polyimide with a thickness of 50 μm. Copper layers 35 of approximately 18 μm thickness are respectively present on both sides of the carrier material 33. Each copper layer 35 is cemented, for example, with the carrier material 33 or directly connected in contact with it. For passivation, each copper layer 35 is provided with a protective lacquer. In the region of the solder points, the copper layers 35 are connected with one another via contactings that run through the carrier material 33.

Flexible circuit boards also can be used for the conductor feed to the choke (direct current feed) of the detuning circuit of the radio frequency antenna, but the flexible circuit boards are separate from the electrical connection with RF antenna function. FIG. 4 shows an exemplary embodiment. The direct current feed ensues via a conductor trace 41 which is attached in an electrical-insulated manner on a radio frequency shield 15C of a gradient coil unit. A flexible circuit board 43 is soldered on the conductor 41 and in turn bends with a curvature radius of approximately 5 mm on an antenna rod 19C sunk approximately 10 mm. There it is soldered with a conductor of the detuning circuit on a width of approximately 4 mm. To protect a choke 45 used in the detuning circuit, this is partially countersunk in the antenna rod 19C and cemented there. The choke is electrically connected with the flexible circuit board.

The electrical connections shown in FIG. 3 and FIG. 4 are resistant to damage of the solder connections, even given high vibration amplitudes and long stress. The electrical components that are mounted corresponding to FIG. 4 are also not destroyed by vibrations. This is the case even given long-duration stress variation in the frequency range up to some kHz. Due to the soldering of the flexible circuit boards in a blind hole or longitudinal slit, large curvature radii that are therewith tolerant of mechanical stresses can be realized in a small space.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance apparatus comprising:
   a magnetic resonance data acquisition unit comprising a basic field magnet and a gradient and radio frequency coil unit;
   said gradient and radio frequency coil unit comprising an antenna rod and a conductor and a gradient coil unit being combined to form a unitary component, and an electrical connection between said conductor and an electrical adjoining contact region of the gradient coil unit in said unitary component; and
   said electrical connection comprising a flexible circuit board having opposite ends respectively electrically connected to said conductor and to said contact region.

2. A magnetic resonance apparatus as claimed in claim 1 wherein said gradient and radio frequency coil unit comprises an antenna circuit in said unitary component, said antenna circuit including said conductor.

3. A magnetic resonance apparatus as claimed in claim 1 wherein said gradient and radio-frequency coil unit comprises a radio frequency shield at least partially surrounding said gradient coil, said radio frequency shield including said contact region.

4. A magnetic resonance apparatus as claimed in claim 1 wherein said gradient and radio-frequency coil unit comprises a detuning circuit, said detuning circuit including said conductor.

5. A magnetic resonance apparatus as claimed in claim 4 wherein said detuning circuit comprises an electrical supply line, and wherein said contact region is a region of said electrical supply line.

6. A magnetic resonance apparatus as claimed in claim 1 wherein said flexible circuit board has a width of less than 10 mm.

7. A magnetic resonance apparatus as claimed in claim 1 wherein said flexible circuit board has a radius of curvature of approximately 5 mm.

8. A magnetic resonance apparatus as claimed in claim 1 wherein said flexible circuit board is comprised of polyimide.

9. A magnetic resonance apparatus as claimed in claim 1 wherein said gradient and radio frequency coil unit comprises an antenna circuit board for said antenna rod in said unitary component, said antenna circuit board comprising an antenna circuit board component that is at least partially countersunk in said antenna circuit board and is fixed to said antenna circuit board.

10. A magnetic resonance apparatus as claimed in claim 1 wherein said electrical connection is a first electrical connection, and wherein said gradient and radio-frequency coil unit comprises a plurality of electrical connections, including said first electrical connection, in said unitary component, each of said plurality of electrical connections being respectively formed by a flexible circuit board.

11. A gradient and radio frequency coil unit for use in a magnetic resonance apparatus, comprising:
    an antenna rod;
    a conductor;
    a gradient coil unit, said antenna rod, said conductor and said gradient coil unit being combined to form a unitary component; and
    an electrical connection between said conductor and an adjoining electrical contact region of said gradient coil unit in said unitary component, said electrical connection comprising a flexible circuit board having opposite ends respectively electrically connected to said conductor and to said contact region.

12. A gradient and radio frequency coil unit as claimed in claim 11 comprising an antenna circuit in said unitary component, said antenna circuit including said conductor.

13. A gradient and radio frequency coil unit as claimed in claim 11 comprising a radio frequency shield at least partially surrounding said gradient coil in said unitary component, said radio frequency shield including said contact region.

14. A gradient and radio frequency coil unit as claimed in claim 11 comprising a detuning circuit in said unitary component, said detuning circuit including said conductor.

15. A gradient and radio frequency coil unit as claimed in claim 14 wherein said detuning circuit comprises an electrical supply line, and wherein said contact region is a region of said electrical supply line.

16. A gradient and radio frequency coil unit as claimed in claim 11 wherein said flexible circuit board has a width of less than 10 mm.

17. A gradient and radio frequency coil unit as claimed in claim 11 wherein said flexible circuit board has a radius of curvature of approximately 5 mm.

18. A gradient and radio frequency coil unit as claimed in claim 11 wherein said flexible circuit board is comprised of polyimide.

19. A gradient and radio frequency coil unit as claimed in claim 11 comprising an antenna circuit board for said antenna rod in said unitary component, said antenna circuit board comprising an antenna circuit board component at least partially countersunk in said antenna circuit board and being fixed thereto.

20. A gradient and radio frequency coil unit as claimed in claim 11 wherein said electrical connection is a first electrical connection, and wherein said gradient and radio frequency coil unit comprises a plurality of electrical connections including said first electrical connection, each of said plurality of electrical connections being formed by a respective flexible circuit board.

* * * * *